United States Patent [19]

Man

[11] Patent Number: Plant 7,038

[45] Date of Patent: Sep. 19, 1989

[54] DISTINCT VARIETY OF BEGONIA PLANT NAMED SANDRA

[75] Inventor: Jan Man, Lisse, Netherlands

[73] Assignee: Oglevee Ltd., Connellsville, Pa.

[21] Appl. No.: 251,656

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

The new cultivar is generally characterized by its strong growth and abundant flowering. The unique soft pink and creamy yellow and orange overtones distinguishes it from the present pink varieties on the market. The bloom is long lasting. The plant is compact with good basal branching and self supporting stems.

1 Drawing Sheet

BACKGROUND OF THE INVENTION

The present invention comprises a new and distinct cultivar of *Begonia*×*hiemalis* known by the varietal name of Sandra. The new cultivar is a selection of a selfing of the white cultivar Paloma (U.S. Plant Pat. No. 6,216). The cultivar is best compared with the cultivar Rosalie (U.S. Plant Pat. No. 6,321). Sandra has the same habit and growing characteristics as Rosalie. It differs from Rosalie in color with Rosalie being a pastel peach with pink tones and Sandra being a very light soft blush pink with slight overtones of creamy yellow and orange.

The new cultivar was discovered in February of 1985 at Limaplant b.v. in Lisse, Holland; was first asexually reproduced by cuttings at Limaplant b.v. in Lisse, Holland and has been repeatedly asexually reproduced by cuttings for Oglevee Ltd. in Connellsville, Pa. It has been found to retain its distinctive characteristics through successive propagations.

The new cultivar is generally characterized by its strong growth and abundant flowering. The unique soft pink and creamy yellow and orange overtones distinguishes it from the present pink varieties on the market. The bloom is long lasting. The plant is compact with good basal branching and self supporting stems.

The new cultivar, when grown in a greenhouse in Connellsville, Pa., has a response time to 9 to 10 weeks from a well-rooted cutting to a flowering finished plant in a six inch pot (no pinch).

DESCRIPTION OF THE DRAWING

The accompanying drawing illustrates a new cultivar, the color being as nearly true as possible with color illustration of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a mixture of 20N-20P-20K. Color readings were taken indoors under 200 foot-candles of cool white fluorescent tubes. Color references are to The R.H.S. Colour Chart of The Royal Horticultural Society of London, unless noted differently.

Botanical classification: *Begonia*×*hiemalis*

Flower:

- *Fully expanded.*—5.5 cm. in diameter; side view; flattened oval appearance.
- *Borne.*—Compound dichasium with opposite bracts at the base of each flower cluster.
- *Bract.*—Obtuse base with a slightly undulate margin, and occur at bifurcation of the inflorescence.
- *Stems.*—Strong and upright; average stem width 0.5 cm. in diameter; color yellow-green group 145C.
- *Form.*—Double. Each flower generally has 2 sepals, 7 petals, 16 petaloids (each group may vary ± 1 structure).
- *Permanence.*—Very long lasting bloom with average life span of 2–3 weeks.

Color:

- *Tonality from a distance.*—Very light soft blush pink with a slight overtones of creamy yellow and orange.
- *Front of petals.*—Fully mature and expanded and are characterized by margin being a color red group 36D and the center of the petal being red group 36C.
- *Reverse of petals.*—Fully mature and expanded and are characterized by a margin with a color red group 36D and inner area having slight orange tones.
- *Base of petals.*—The base of each disected petal has a translucent center with its sides being the color of orange group 27B.
- *Throat.*—None.
- *Calyx.*—Consists of two sepals (outer floral envelopes). Front Calyx — Red group 36C and as you move toward the base of the petal, slight tones. Red group 49C. Reverse of Calyx — This flower part in the bud stage has a more intense color than mature, fully expanded reverse of petal. The color of calyx in the bud stage is characterized by the color at the tip of the margin, red group 36C. The rest of the sepal appears a creamy translucent color. Other Comments — Flower color tends to be lighter, almost translucent on the outer edges of a mature flower while its center has slight overtones of soft yellow. Immature and not fully expanded petals are characterized by a color of creamy very light yellow and have not yet begun to display its pink hues.

Petals:

*Texture.*—Crepe paper like (gentle crinkles).

*Appearance.*—Oval, with color gradient. Outer edge translucent light pink with yellow overtones.

*Arrangement.*—Fully double due to the presence of 16 petaloids.

*Persistence.*—Very good flower response produces high number of buds.

*Fragrance.*—None observed.

Reproductive organs: All reproductive organs have modified into petaloids. Anthers, filament, pollen, style and ovaries could not be observed. The outer part of the petaloids is almost translucent while its base is color orange group 27B.

Plant:

*Form.*—Semi-short, compact internodes (4–5 cm. apart); upright; good self-support strength, good basil branching.

*Growth.*—Vigorous.

*Height from soil line.*—25–35 cm. in 10 weeks (no pinch, no cycocel).

*Spread.*—28–34 cm: in 10 weeks (no pinch, no cycocel).

Foliage:

*Size.*—Average length of 16 cm. and average width of 11 cm. for mature leaf 5 nodes up from the base of the stem.

*Quantity.*—Very abundant.

*Shape.*—Acute tip with irregularly lobed attachment; edge is slightly doubly serrate.

*Top side.*—Green group 137B; shiny and smooth.

*Underside.*—Green group 148C; shiny and smooth.

*Ribs and veins.*—Smooth on top side, raised on lower side, lower side veins only area on leaf where visible tricomes (hairs) appear.

*Rib and vein color.*—Top side: green group 150D; bottom: yellow-green group 147D.

*Margin.*—None.

*Stipules.*—Color yellow-green group 145C.

I claim:

1. A new and distinct variety of begonia characterized by its strong growth, abundant flowering, unique color of soft pink with creamy yellow and orange overtones, long lasting, compact plant with good basal branching and self supporting stem as herein shown and described.

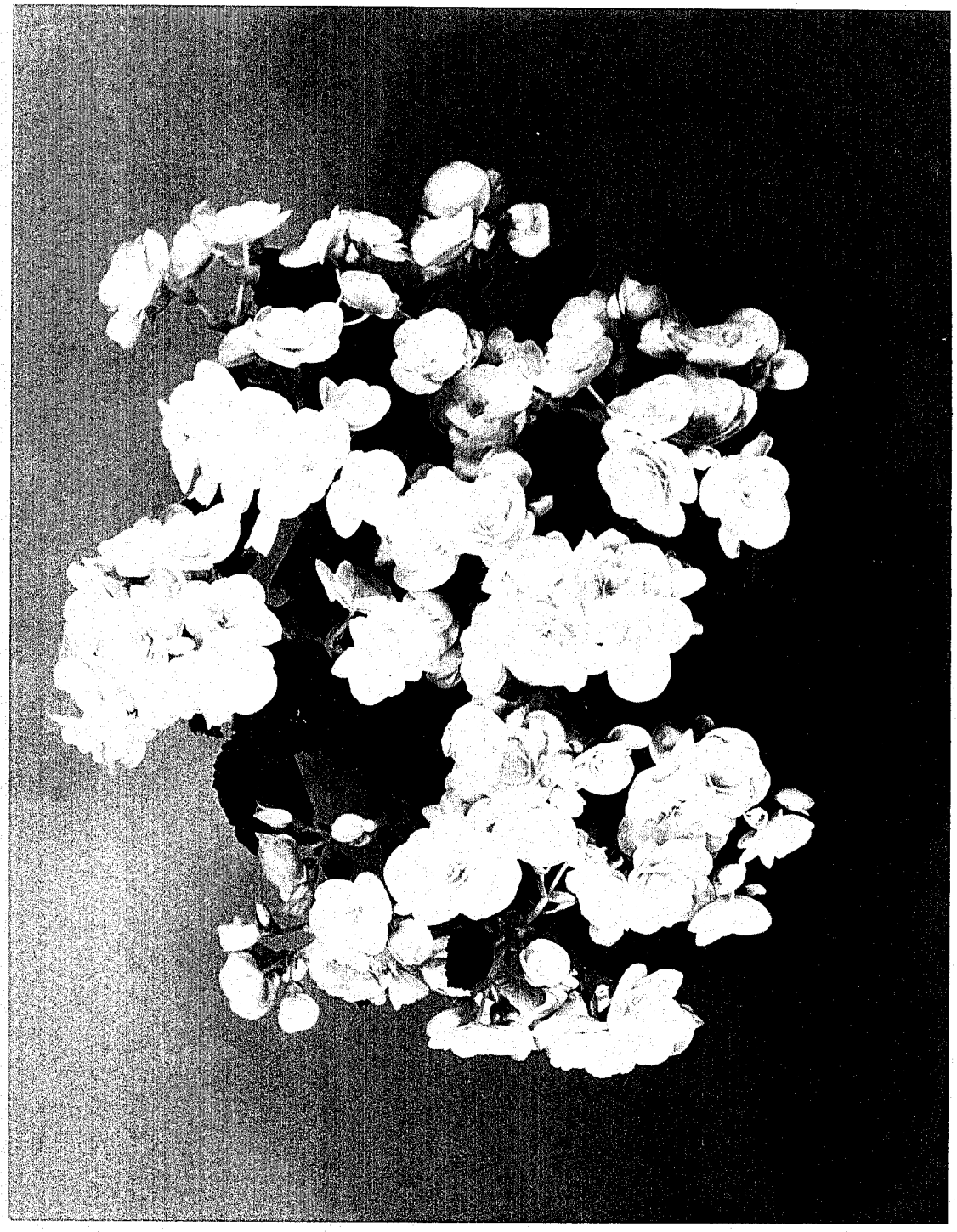

* * * * *